United States Patent
Hirose et al.

(10) Patent No.: US 8,303,980 B2
(45) Date of Patent: Nov. 6, 2012

(54) WOUND-DRESSING MATERIAL AND METHOD FOR MANUFACTURING THE SAME

(75) Inventors: Kaoru Hirose, Tokyo (JP); Hiraku Onishi, Tokyo (JP); Yoshiharu Machida, Tokyo (JP)

(73) Assignees: Hoshi Pharmaceutical Co., Ltd., Tokyo (JP); Hoshi University, Tokyo (JP)

( * ) Notice: Subject to any disclaimer, the term of this patent is extended or adjusted under 35 U.S.C. 154(b) by 1212 days.

(21) Appl. No.: 11/271,903

(22) Filed: Nov. 14, 2005

(65) Prior Publication Data

US 2006/0286156 A1 Dec. 21, 2006

(30) Foreign Application Priority Data

Jun. 20, 2005 (JP) ................................. 2005-179617

(51) Int. Cl.
*A61F 13/00* (2006.01)
(52) U.S. Cl. ........................................ 424/443; 424/445
(58) Field of Classification Search .................. None
See application file for complete search history.

(56) References Cited

U.S. PATENT DOCUMENTS

| | | | | |
|---|---|---|---|---|
| 5,597,581 A | * | 1/1997 | Kaessmann et al. | 424/449 |
| 5,836,970 A | * | 11/1998 | Pandit | 606/213 |
| 6,187,324 B1 | * | 2/2001 | Ogi et al. | 424/401 |
| 2003/0113387 A1 | | 6/2003 | Tsuchida et al. | |
| 2005/0042265 A1 | | 2/2005 | Guillot et al. | |

FOREIGN PATENT DOCUMENTS

| | | | |
|---|---|---|---|
| JP | 50-160414 | | 12/1975 |
| JP | 59-104321 A | | 6/1984 |
| JP | 59-205324 A | | 11/1984 |
| JP | 2000-281696 A | | 10/2000 |
| JP | 2003012494 A | * | 1/2003 |
| JP | 2003-201247 | | 7/2003 |
| JP | 2003-265591 | | 9/2003 |
| JP | 2004091335 A | * | 3/2004 |
| JP | 2004091335 A | * | 3/2004 |
| JP | 2004-231604 | | 8/2004 |
| WO | 02/07745 A1 | | 1/2002 |
| WO | 03/068281 A1 | | 8/2003 |

\* cited by examiner

*Primary Examiner* — Anand Desai
*Assistant Examiner* — Melissa Mercier
(74) *Attorney, Agent, or Firm* — Birch, Stewart, Kolasch & Birch, LLP.

(57) ABSTRACT

A wound-dressing material being a product comprising chitosan as a base material and kumazasa extract, and a method for manufacturing the wound-dressing material by gelatinizing a mixture solution containing chitosan and kumazasa extract and drying the resulting gel. The wound-dressing material can be applied to humans and animals, and have biocompatibility, antibacterial effects, and low toxicity, and also have flexibility to be formed into various shapes for applying for various wounds.

7 Claims, 2 Drawing Sheets

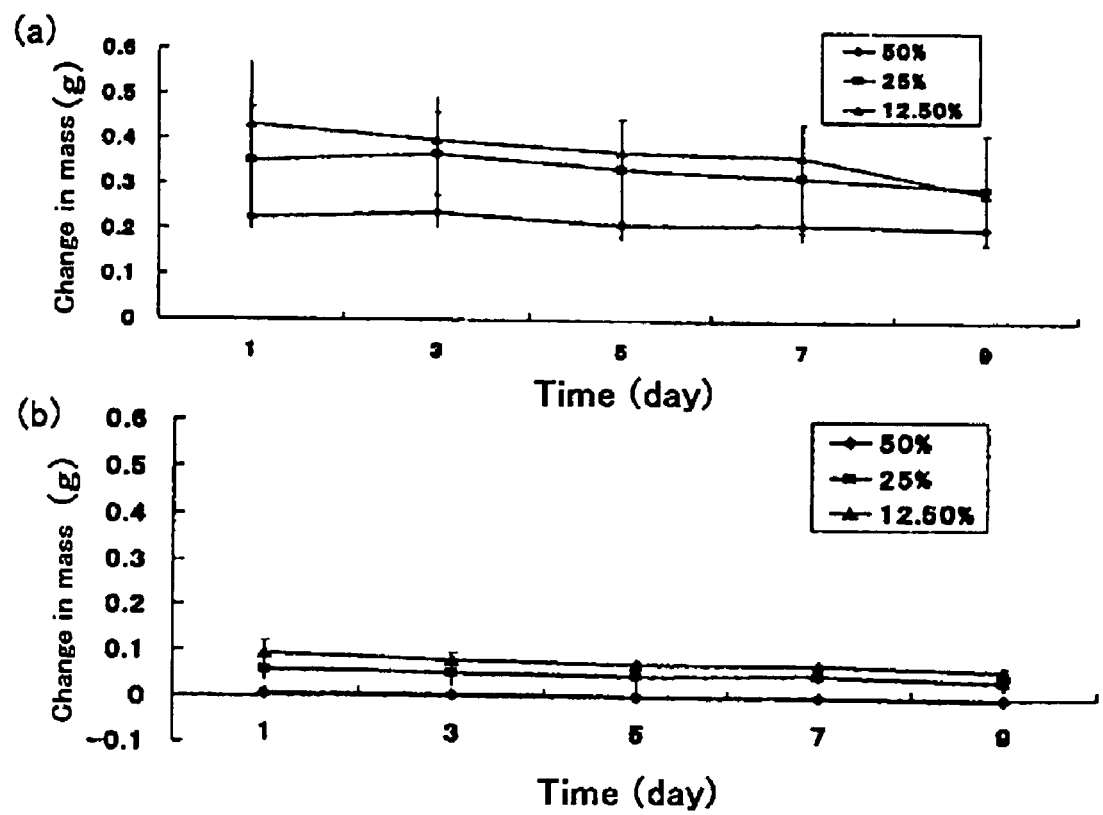

WOUND-DRESSING MATERIAL AND METHOD FOR MANUFACTURING THE SAME

BACKGROUND OF THE INVENTION

1. Field of the Invention

The present invention relates to wound-dressing materials and methods for manufacturing the same. Specifically, the present invention relates to wound-dressing materials suitable for healing the wounds such as traumas, burns, frostbites, ulcers, and bedsores.

2. Description of the Related Art

Recently, in treatment of traumatic skin lesions such as traumas, burns, frostbites, ulcers, and bedsores, formation of granulation tissue has been enhanced by using wound-dressing materials for keeping environments of wound surfaces moist to regenerate normal skins at the wound sites. In the present commercially available wound-dressing materials, a wide variety of raw materials, i.e. animal-derived materials such as chitin, synthetic materials, and plant-derived materials such as alginic acid, are used. Compositions of each wound-dressing material are determined depending on subjects to be healed. Namely, the wound-dressing material is determined in consideration of the conditions of the wound and the characteristics of the wound-dressing material.

Examples of ingredients of the wound-dressing materials include animal-derived materials such as chitin and chitosan. Chitin and chitosan are natural polysaccharide macromolecules, and have biocompatibility, degradable properties, and low toxicity. Therefore, the wound-dressing materials made of these materials have biocompatibility effective to traumas such as burns. Chitin and chitosan are also used for other purposes than for the wound-dressing materials. Yaizu Suisankagaku Industry Co., Ltd. produces low-molecular chitin and chitosan as a sweetener for functional foods (Japanese Unexamined Patent Application Publication No. 2000-281696) and chitosan as a food additive (trade name: Chito-Clear) having antimicrobial properties. Snow Brand Milk Products Co., Ltd. uses chitosan as a stabilizer for foods such as Dole fruits and cheesecake.

Chitin and chitosan are different from each other in the following points. Structurally, chitin is synonymous with chitosan having an acetylated amino group, characteristically, chitin is insoluble in acids, alkalis, and organic solvents that are commonly used, but chitosan is soluble in dilute hydrochloric acid and dilute acetic acid. Beschitin (registered trademark No. 2130021) is a sheet-type chitin-derived wound-dressing material. Since the dressing material containing chitin has biocompatibility, it is effective to traumas such as burns. Besides chitin, a cellophane-like membrane having a high organic affinity and adhesion is formed by thinly spreading a chitosan solution and drying it. It has been confirmed that the chitosan membrane has antibacterial properties and is superior in healing of sores, absorption of exudates, and flexibility [Tachihara, K., Onishi, H., Machida, Y., et al., Evaluation of membranes of chitin, chitosan, and a chitin-chitosan mixture as a burn-dressing material, Yakuzaigaku (Pharmacology), 1997, 57(1), 40-49; Tachihara, K., Onishi, H., Machida, Y., et al., Preparation of silver sulfadiazine-containing sponge membranes of chitosan and a chitin-chitosan mixture and their evaluation as burn-dressing materials, Yakuzaigaku (Pharmacology), 1997, 57(3), 159-167].

It is known that dressing materials of polymers are more effective to chronic wounds. Chronic wounds are defined as wounds that are not sufficiently repaired by a normal mechanism, and are typical phenomena caused by basic disorders such as diabetes, vascular disease, and circulatory disorders in bedridden patients. Therefore, the chronic wounds are classified into bedsores (decubitus), venous ulcers, and diabetic ulcers according to the basic disorders that cause the chronic wounds. Various types of treatments and materials are used according to the causes of disorders in order to deal with various types of disorders and to enhance the healing of wounds. In healing of the chronic wounds that are difficult to be healed, it is known that dressing materials of chitosan polymers having characteristics of providing moist environment for the wounds are more effective than absorptive gauze mainly used in conventional treatment.

Recently, the healing of relatively mild wounds such as burns and traumas have been remarkably developed, and various dressing materials and methods for the healing have been studied. The materials are mainly classified into synthetic materials and biomaterials. Examples of the synthetic materials include polyurethane films, for example, Tegaderm (3M Health Care, Ltd.), Opsite Wound (Smith & Nephew plc.), IV3000 (Smith & Nephew plc.), and Bioclusive (Johnson & Johnson Co.,); polyurethane forms, for example, Hydrosite (Smith & Nephew plc.); and hydrocolloids, for example, DuoActive (Convatec Co.), Comfeel (Coloplast Co.), Tegasorb (3M Health Care, Ltd.), and Absocure (Nitto Medical Corp.). Examples of the biomaterials include alginate dressing materials made of alginic acid, for example, KaltoStat (Convatec Co.), Sorbsan (Alcare Company), Algoderm (Medicon, Inc.), and Kurabio AG (Kuraray Co., Ltd.); and chitin fiber sheets, for example, Beschitin (Unitika).

Leaves of kumazasa (scientific name: *Sasa albomarginata* or *Sasa veitchii*, Genus: *Sasa*, Family: Gramineae) are widely used as wrapping materials of foods because of antibacterial and antiseptic effects thereof. Various activities including antiulcer effects, antitumor effects, anti-inflammatory effects, sedating effects, detoxification effects, and diuretic effects are confirmed by pharmacological studies. Additionally, it has been recently reported that Kumazasa extract produced by Hoshi Seiyaku K. K. has antiulcer effects against stress ulcers, pylorus ligation ulcers (ulcers caused by gastric acid), and drug-induced ulcers due to aspirin, caffeine, or the like. Antitumor effects and cell repair-enhancing effects are also reported. Furthermore, kumazasa extract is directly applied to burn and wound sites with the intention to utilize the activities for regeneration of epithelial and muscular tissues and the antiseptic and antitumor effects. The effects of this are confirmed.

SUMMARY OF THE INVENTION

Wound-dressing materials using chitin as a raw material problematically cause liquefaction in severe wounds. Therefore, sufficient protection effects for wounds cannot be expected. A chitosan membrane made by thinly spreading a chitosan solution and drying it, as shown in above-mentioned non-patent documents, does not exhibit good results in a reducing rate of wound sites. In addition, dressing materials for the medical uses made of chitosan membranes containing materials having antibacterial and antiulcer effects have been investigated, but the practical use is not yet achieved.

In severe wounds, for example, in bedsores, significant losses of epidermis and also of granulation occur. This causes deep irregular scars and abundant exudates, so it is difficult to treat such wounds by using the above-mentioned commercially available dressing materials that are generally used for mild wounds. For example, since synthetic materials cannot sufficiently absorb exudates, the exudates accumulate on the wound surfaces, resulting in a decrease of the healing speeds.

Absorption of exudates by biomaterials is relatively sufficient. However, the adhesion to the wound surfaces is insufficient, so liquefaction due to the exudates frequently occurs. Therefore, actually, sufficient protective effects cannot be expected. With the above-mentioned reasons, in the present medical field, severe wounds are still healed by removing the exudates, sterilizing, and drying; i.e. the severe wounds are sufficiently dried and Japanese Pharmacopoeia gauze to which ointments containing antibacterial agents are applied is mainly used.

Accordingly, it is an object of the present invention to provide wound-dressing materials for humans and animals and methods for manufacturing the same. The wound-dressing materials have biocompatibility, antibacterial effects, and low toxicity, and have flexibility to be formed into various shapes. Thus, they can be applied to various wounds.

The inventors have made various studies in order to overcome the drawbacks and found that the drawbacks can be overcome by a wound-dressing material of a combination of chitosan and kumazasa extract; thus, the present invention has been completed.

Namely, the wound-dressing material according to the present invention is a product containing chitosan as a base material and kumazasa extract.

The wound-dressing material according to the present invention preferably includes the kumazasa extract at a content of 6 to 60 mass %. A sheet-shaped product and a product containing polyethylene glycol are also preferable.

A method for manufacturing the wound-dressing material according to the present invention includes gelatinizing of a mixture solution containing chitosan and kumazasa extract and drying of the resulting gel.

In the method for manufacturing the wound-dressing material according to the present invention, the gel is preferably obtained by adding an acetic acid solution to the mixture solution. More preferably, the drying is performed by natural drying or freeze drying.

The wound-dressing material according to the present invention includes chitosan having high biocompatibility and kumazasa extract having an antibacterial effect, an antiulcer effect, and a cell repair-enhancing effect, and can enhance the regeneration of epithelial and muscular tissues with low toxicity. The method for manufacturing the wound-dressing material according to the present invention can provide the wound-dressing material so as to be formed into a desired size and to be applied to various wounds of humans and animals. Therefore, it is possible to provide drug products for healing traumas, burns, frostbites, ulcers, and bedsores.

BRIEF DESCRIPTION OF THE DRAWINGS

FIG. 3 is a graph showing water absorbing properties of the wound-dressing material according to the present invention.

DESCRIPTION OF THE PREFERRED EMBODIMENTS

Figure 1:
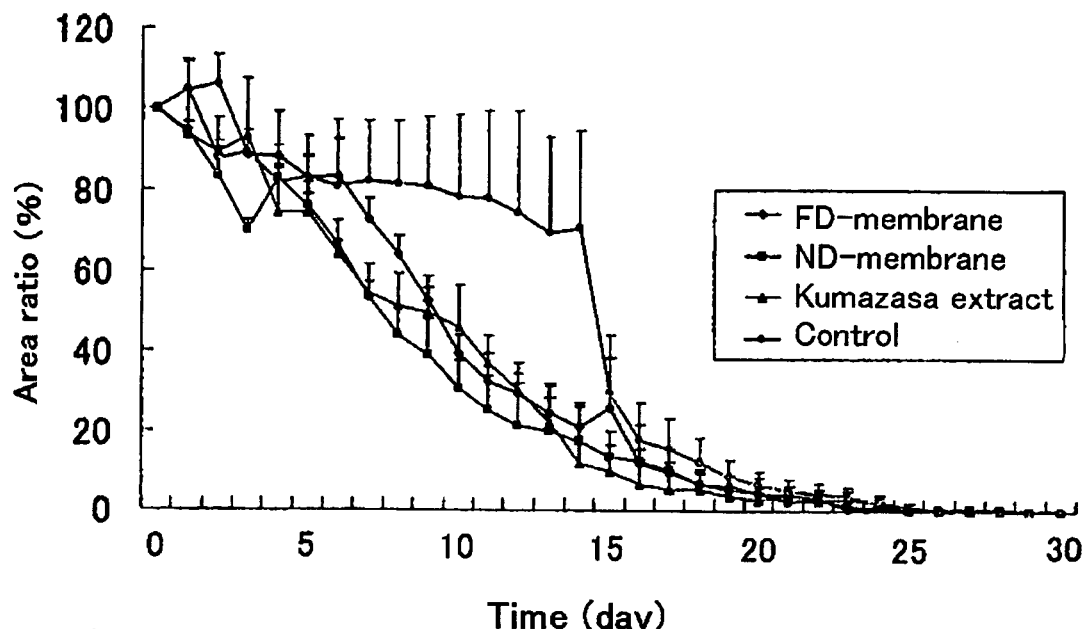
FIG. 1 is a graph showing changes in areas of the wound surfaces in model rats of frostbites when the wound-dressing material according to the present invention was applied.

The preferred embodiments of the present invention will now be described in detail.

The wound-dressing material according to the present invention includes kumazasa extract as an active ingredient. Kumazasa used in the present invention and the extraction processes of the same do not have any limitation. The extraction processes can be performed according to a method generally used for the extraction from plants. For example, kumazasa extract can be obtained by immersing kumazasa in an extraction solvent or heating kumazasa to reflux, and concentrating or without concentrating the resulting extraction after filtration. The concentrated or dried extraction may be dissolved in the solvent again. Any extraction solvent which is generally used as an extraction solvent can be used without any limitation. Examples of the solvent include water or organic solvents such as methanol, ethanol, acetone, ethyl acetate, 1,3-butylene glycol, and propylene glycol. Any one of these solvents or any combination of two or more of these solvents can be used. The conditions for the extraction do not have any limitation.

Kumazasa extract can be suitably prepared by the following processes. First, leaves of kumazasa are dried and cut into small pieces, and are then immersed into water. The water is boiled to extract water-soluble components and to concentrate if necessary. Then, the concentrated water is boiled under a high pressure for a second extraction and concentration. The conditions suitable for boiling are as follows: a pressure of about 7 atm; a boiling temperature of an effective temperature lower than an alteration temperature of caramel (i.e. 200° C.), for example, about 120 to 160° C.; and a boiling period of 6 to 12 hours (see Japanese Unexamined Patent Application Publication No. 50-160414). With this heating extraction process under a high pressure, a high extraction temperature can be achieved. Therefore, active ingredients (polysaccharides) of kumazasa can be effectively extracted and concentrated without using a specific solvent.

Instead of increasing the boiling point under a high pressure as in the above, the boiling temperature can be increased by raising the boiling point by charging a solvent, for example, overheated water vapor of 120 to 160° C., sodium hydrogen carbonate, or air (see Japanese Unexamined Patent Application Publication No. 59-205324). In the second concentration process in the above, a method for obtaining effective ingredients can be suitably performed by concentrating a solution already concentrated twice, and boiling the resulting solution with addition of hot water. Then, the supernatant is yielded and concentrated. The concentrated supernatant is cooled to precipitate the effective ingredients (see Japanese Unexamined Patent Application Publication No. 59-104321).

Examples of the commercially available kumazasa extract that can be preferably used include Kumazasa Ekisu (Hoshi Seiyaku K. K.). Since Kumazasa Ekisu is produced by effectively extracting active ingredients (polysaccharides) contained in kumazasa and is also eliminated risks such as agricultural chemicals and heavy metals to a minimum, it is highly safe and effective as a healing product for applying to a living body.

The wound-dressing material according to the present invention includes chitosan as a base material. Chitosan used in the present invention can be produced by a method generally used, without any limitation. For example, chitosan can be obtained by deacetylation of chitin in an alkaline solution of a high concentration. Chitin can be obtained by deproteinization of crab shell in a dilute alkaline solution of a sodium hydroxide or the like, and by removing calcium in a dilute acid solution of hydrochloric acid or the like. The viscosity of chitosan according to the present invention is, but not limited to, preferably 300 to 3000 cps, more preferably 800 to 1500 cps in a solution containing 0.5% acetic acid and 0.5% chitosan. The deacetylation degree of chitosan is, but not limited to, preferably 75 mol % or more, more preferably 75 to 90 mol %.

The wound-dressing material of the present invention contains kumazasa extract and chitosan as essential components, and may contain additives and the like if necessary. For example, addition of a plasticizer can improve the plasticity. Polyethylene glycol (PEG) is a preferable plasticizer. The molecular weight and content of PEG are determined based on the desired plasticity. Generally, the molecular weight is preferably 100 to 2000, more preferably 150 to 500; and the combination ratio (PEG/chitosan) is preferably 2:3 to 1:50, more preferably 1:2 to 1:10. When a ratio of PEG is lower than the range, sufficient plasticity may not be obtained. On the other hand, the effects of kumazasa extract and chitosan may be decreased when a ratio of PEG is higher than the range.

The content of kumazasa extract of the wound-dressing material according to the present invention is preferably 6 to 60 mass %, more preferably 12.5 to 50 mass %. When content is lower than the range, the effects of the kumazasa extract on wound healing may be insufficient in some instances. On the other hand, when content is higher than the range, problems in preparation, such as absorbency, may occur in some instances and the manufacturing cost is also increased. The wound-dressing material according to the present invention is preferably formed into a sheet-type product. It is preferable to determine the shape of the product based on wound surface conditions, but the sheet-type product can be applied to various wound surfaces.

The wound-dressing material according to the present invention enhances formation of granulation and formation of epidermal tissues by antibacterial and wound-protective effects of chitosan and by antibacterial, anti-inflammatory, antiulcer, and cell repair-enhancing effects of kumazasa extract; thus, and healing-enhancing effects, which previously have not been obtained, can be achieved by synergistic effects thereof. When conventional wound-dressing materials are applied to wound surfaces in the middle period of healing, necrosis and scab are frequently removed for enhancing anagenesis in the retention of moist by the wound-dressing materials. On the other hand, the wound-dressing material according to the present invention can prevent the generation of necrosis and scab in the middle period of healing by the antibacterial, anti-inflammatory, and wound-protective effects and can keep the moist environment clean; thus, a great cell repair-enhancing effect is achieved.

The wound-dressing material according to the present invention can be applied for healing of both mild wounds such as burns and severe wounds such as bedsores. The healing of bedsores by the wound-dressing material of the present invention is better than that by conventional wound-dressing materials. In bedsores, subcutaneous tissues tend to be lost due to epidermal lesions or loss or granulation loss. Therefore, the wound-dressing material of the present invention, which has the antibacterial effect and cell repair-enhancing effect, is more effective. Since many of the conventional wound-dressing materials are not superior in absorbency, they are difficult to be applied to bedsores in period of requiring absorption of exudates or antibacterial activities. However, the wound-dressing material of the present invention is superior in absorbency to be suitably applied to such bedsores.

The manufacturing of the wound-dressing material according to the present invention can be performed by known chitosan-processing methods, without any limitation. The following method is preferable.

The method for manufacturing the wound-dressing material of the present invention is performed by gelatinizing a mixture solution containing chitosan and kumazasa extract and drying the resulting gel. The method for gelatinizing the mixture solution does not have any limitation, but it can be preferably performed by adding an acetic acid solution and stirring. The concentration of the acetic acid solution is preferably about 2% (v/v).

The resulting gel can be preferably dried by natural drying or freeze drying. The wound-dressing material of the present invention obtained by natural drying or freeze drying exhibits a high absorbency and an increase in the healing speed to enhance the absorption of exudates and the healing of the sore; thus, the wound surfaces are favorably cured. The resulting gel can be processed into various shapes by putting the gel in a mold having a desired shape and drying it; thus, the shape can be determined to be suitable to the wound.

EXAMPLES

The present invention will now be further specifically described with reference to the examples, but the present invention is not limited to these examples.

Preparation of Wound-Dressing Material

Kumazasa extract (Hoshi Seiyaku K. K.) extracted by hot-water extraction was mixed with chitosan (viscosity: 800 to 1500 cps, deacetylation degree: 75 to 90 mol %) at a content of 50, 25, and 12.5 mass %. Then, 2% (v/v) acetic acid solution was added to the mixture for gelatinization. After the gelatinization, the gel was degassed under a reduced pressure for 30 minutes. Then, the gel was poured into a mold of Teflon®, and dried. The drying was performed by freeze drying for overnight or by natural drying at room temperature for 2 days. The membrane produced by the freeze drying is referred to as FD-membrane, and the membrane produced by the natural drying is referred to as ND-membrane.

Application to Fostbite Model Rat

Frostbite model rats used in examples were prepared by as follows: Seven-week old Wistar male rats were each anesthetized by intraperitoneally injecting with a solution of 0.12 mL of sodium pentobarbital diluted with saline to 0.5 mL. Skin of a 1.5 cm diameter circle having a center at 1.5 cm right from the center line under back shoulder blade was removed from each of the rats. Then, the exposed tissue surface site of the rat was pressed with a brass tube (thickness: 1.5 mm, bottom face diameter: 1.5 cm) entirely cooled by filling with dry-ice/acetone with setting a household polyethylene film between the surface and the brass tube for 3 minutes. The site treated as above was protected by securing with medical nonwoven gauze for overnight. Then, the wound surface was washed with saline after 24 hours from the forming of the frostbite, and a drug product or gauze cut into 2 cm×2 cm was applied to the wound surface.

In the above-described preparation of the frostbite model rats, the frostbites were directly formed on muscle tissues after removing skin. Therefore, blood flow is blocked to cause tissue necrosis. Since the necrosed tissues are completely removed, the wound surfaces have irregularity. Since bedsores are caused by necrosis of epidermal tissue and subcutaneous cells by blocking of blood flow, the wound surfaces have irregularity. The frostbite models have wound surfaces and wound conditions highly similar to those of bedsores, so the frostbite models can be suitably used as a bedsore model.

Tests were performed by applying two-ply gauze (Japanese Pharmacopoeia) (referred to as Control group); an FD-membrane containing 50% kumazasa extract and a piece of untreated gauze on the FD-membrane (referred to as FD-membrane group); an ND-membrane containing 50% kumazasa extract and a piece of untreated gauze on the ND-membrane (referred to as ND-membrane group); or a piece of gauze containing 0.3 mL of kumazasa extract and a piece of untreated gauze on the gauze (referred to as Kumazasa extract group) to the wound surfaces of the rats after washing with saline. The wound surfaces covered with the drug products or gauze were secured with tape. The drug products and gauze were changed everyday. Three samples (n=3) were used in each group.

The effects of the products and gauze on the frostbite model rats were evaluated as follows:

1. Adhesion of Product

The adhesion of the membranes was measured over 20 days based on an amount of saline used in removing each membrane from the wound surface. The amount of saline was determined by measuring the volume of saline used when saline was dropped with a syringe by 0.05 mL each time to the drug product or gauze adhered to the wound surface till the drug product or gauze was readily removed from the wound surface with tweezers without applying force. Adhesion was evaluated based on the following criteria. Table 1 shows the results. Table 2 shows moisture contents (mL).

TABLE 1

| | Time (day) | | | | | |
|---|---|---|---|---|---|---|
| | 1 | 5 | 10 | 15 | 20 | 25 |
| Control group | +++ | +++ | ++ | − | N.D. | N.D. |
| | +++ | − | − | − | + | − |
| | ++ | − | − | − | − | − |
| FD-membrane group | +++ | +++ | +++ | + | − | N.D. |
| | + | ++ | +++ | − | ++ | − |
| | + | +++ | +++ | − | − | N.D. |
| ND-membrane group | + | +++ | +++ | − | +++ | + |
| | +++ | +++ | +++ | − | − | N.D. |
| | ++ | + | +++ | − | + | N.D. |
| Kumazasa extract group | + | + | +++ | − | − | − |
| | +++ | +++ | +++ | − | − | N.D. |
| | +++ | +++ | +++ | − | N.D. | N.D. |

+++: use of 0.3 mL or more of saline
++: adhesion of only the center of the wound surface
+: no adhesion
−: dried
N.D.: not detected because of full healing of the wound surface

TABLE 2

| | Time (day) | | | | | |
|---|---|---|---|---|---|---|
| | 1 | 5 | 10 | 15 | 20 | 25 |
| Control group | 0.2 | 0.4 | 0.1 | 0 | N.D. | N.D. |
| | 0.1 | 0 | 0 | 0 | 0.05 | 0 |
| | 1.5 | 0 | 0 | 0 | 0 | 0 |

TABLE 2-continued

| | Time (day) | | | | | |
|---|---|---|---|---|---|---|
| | 1 | 5 | 10 | 15 | 20 | 25 |
| FD-membrane group | 0.3 | 0.4 | 0.35 | 0.1 | 0 | N.D. |
| | 0.2 | 0.1 | 0.3 | 0 | 0.05 | 0 |
| | 0.2 | 0.3 | 0.3 | 0 | 0.1 | N.D. |
| ND-membrane group | 0.1 | 0.1 | 0.3 | 0 | 0.1 | 0.01 |
| | 1.8 | 0.3 | 0.1 | 0 | 0 | N.D. |
| | 0.25 | 0 | 0.2 | 0 | 0 | N.D. |
| Kumazasa extract group | 0.6 | 0 | 0.2 | 0 | 0 | 0 |
| | 0.2 | 0.1 | 0.25 | 0 | 0 | N.D. |
| | 0.1 | 0.2 | 0.2 | 0 | N.D. | N.D. |

In Control group, the adhesion was decreased after the formation of scab. In FD-membrane group, ND-membrane group, and Kumazasa extract group, the adhesion was decreased as the healing proceeded, but was favorable when exudates were secreted from the wound sites.

2. Exudate Absorption by Drug Product

Size of adhesion area of the drug product or gauze to the wound site, change in color of the drug product before peeling, and change in color of the adhered face of the drug product after peeling were visually observed every 24 hours. The results were evaluated based on the following criteria.

Table 3 shows the results. Table 4 shows the changes in color. The color of all drug products before the application was brown.

TABLE 3

| | Time (day) | | | | | |
|---|---|---|---|---|---|---|
| | 1 | 5 | 10 | 15 | 20 | 25 |
| Control group | + | +++ | + | − | N.D. | N.D. |
| | + | − | − | +++ | ++ | − |
| | + | − | − | − | − | − |
| FD-membrane group | ++ | +++ | ++ | + | − | N.D. |
| | + | +++ | + | ++ | +++ | − |
| | +++ | + | ++ | ++ | + | N.D. |
| ND-membrane group | +++ | +++ | + | + | +++ | +++ |
| | + | ++ | +++ | + | − | N.D. |
| | +++ | +++ | +++ | + | + | N.D. |
| Kumazasa extract group | +++ | ++ | ++ | ++ | + | − |
| | ++ | +++ | +++ | − | − | N.D. |
| | ++ | +++ | + | − | N.D. | N.D. |

+++: change into black before peeling
++: change into dark brown at the adhered face after peeling
+: slightly wet with exudates at the wound surface after peeling
−: dried
N.D.: not detected because of full healing of the wound surface

TABLE 4

| | Time (day) | | | | | |
|---|---|---|---|---|---|---|
| | 1 | 5 | 10 | 15 | 20 | 25 |
| FD-membrane group | No change | Black | Slight change of color | No change | N.D. | N.D. |
| | No change | No change | No change | Black | No change | No change |
| | Black | Black | Black | Dark brown | No change | N.D. |
| ND-membrane group | Black | No change | Black | No change | No change | No change |
| | No change | No change | Black | No change | No change | N.D. |
| | No change | No change | Black | No change | No change | N.D. |
| Kumazasa extract group | White | White | White | White | White | No change |
| | White | White | White | No change | No change | N.D. |
| | White | White | White | No change | N.D. | N.D. |

In Control group, exudates were decreased on and after the fifth day because of the formation of scab. In FD-membrane group, ND-membrane group, and Kumazasa extract group, absorption of exudates were favorable. As shown in Table 4, the color of the drug product of Kumazasa extract group was bleached and changed into white at the site adhered with the wound. On the other hand, in FD-membrane group and ND-membrane group, the change in color was slight as a whole. This shows that Kumazasa extract group not containing chitosan has low retention capability and that FD-membrane group and ND-membrane group containing chitosan have high retention capability.

3. Change in Wound Area

Size of the wound area was measured over 20 days, and area ratio was calculated by the following formula:

Area ratio=(length×width of wound site at an observation point)/(length×width of the wound site at the drug product application point); thus, conditions of healing were observed. FIG. 1 shows the results.

With FIG. 1, in FD-membrane group, ND-membrane group, and Kumazasa extract group, a sharp decrease in the area ratio was observed on and after the sixth day from the application of the drug product. This shows that they have effects for greatly enhancing the wound healing in the middle period of the healing. The wounds were healed earlier in ND-membrane group, FD-membrane group, Kumazasa extract group, and then Control group in this order. With regard to the conditions of the wound surfaces, ND-membrane group exhibited an adequate absorption of exudates and healing of sore; thus, the wound surfaces were favorably cured.

Investigation of Drug Product Characteristics

4. Absorption and Strength of Drug Product

Figure 2:
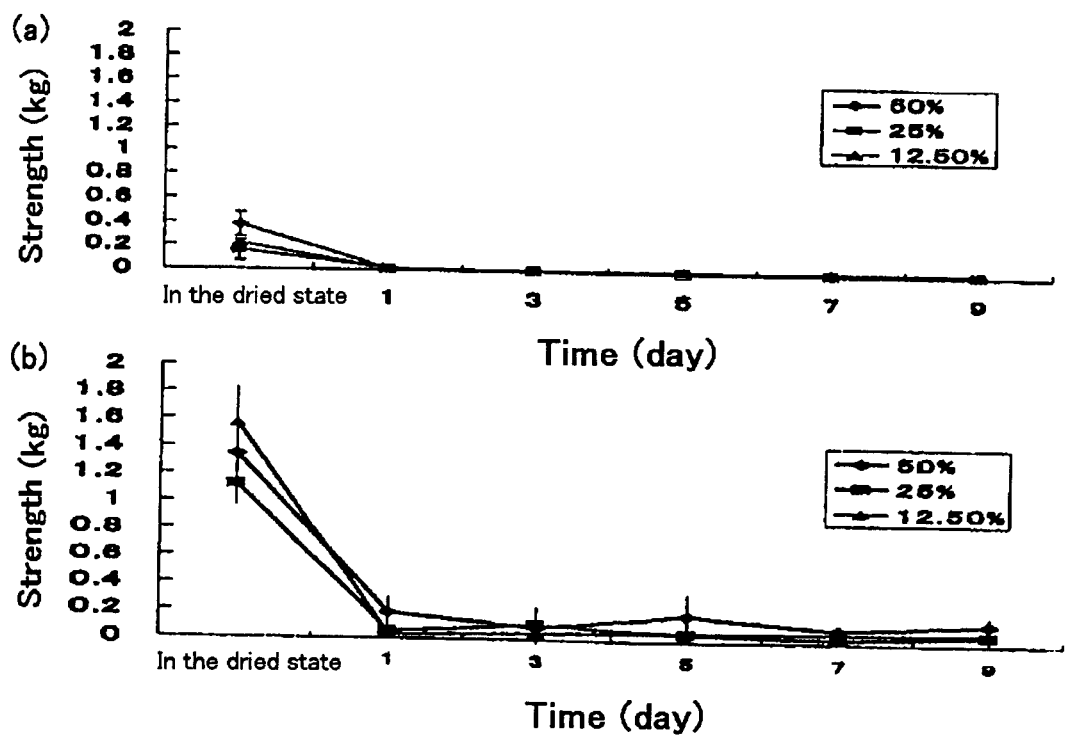
FIG. 2 is a graph showing strength of the membranes of the wound-dressing material according to the present invention.

The membranes cut into rectangular pieces (4.0 cm×0.5 cm) were incubated in a phosphate buffer solution (PBS, pH 7.4) at 37° C. for 9 days. The pieces were taken out every two days to measure the membrane strength and absorption. The strength of the membranes was evaluated by measuring tensile strength, and the absorption was evaluated by measuring a change in mass. The measurement was performed by using a rheometer (NRM-2002D-D, Fudo Industries, Co., Ltd.) at a temperature of 20° C. and a humidity of 40% to 50%. FIGS. 2 and 3 show the results of membrane strength and absorption, respectively.

FIG. 2A shows the results of FD-membrane group and FIG. 2B shows the results of ND-membrane group. In both membranes, differences in strength were observed between the membranes having a kumazasa extract content different from each other when the membranes were dried, but not observed after absorption. FIG. 3A shows the results of FD-membrane group and FIG. 3B shows the results of ND-membrane group. In both membranes, differences in absorption were observed between the membranes having a kumazasa extract content different from each other, and absorption was higher in 12.5%, 25%, and 50% kumazasa extract contents in this order. This suggests that swelling property of the membrane highly depends on absorption property of chitosan. In the comparison between the FD-membrane group and ND-membrane group, absorption property of FD-membrane group was superior to that of ND-membrane group. This suggests FD-membrane is suitable for wounds highly secreting exudates.

Investigation of Drug Product Plasticity

Polyethylene glycols having a molecular weight of 200 and 1000 were used as a plasticizer at a combination ratio (PEG/chitosan) of 9:21 or 1:29. Drug products containing 50% kumazasa extract content to chitosan were prepared as in the above. Control not containing PEG was also prepared. The plasticity was evaluated by measuring strength necessary for deforming the drug products. Specifically, each drug product cut into rectangular pieces (40 mm×20 mm), and the drug product pieces were fixed on a table so that the half of each drug product piece was on the table and the other half of the drug product piece protruded from the table. A plumb was loaded on the protruding end of the drug product piece, and the mass of the plumb when the protruding half formed a right angle to the half on the table, i.e. when the drug product was perpendicular to the ground, was compared. The plasticity increases as a decrease in mass of the loaded plumb. The tests were performed four times in each drug product. Table 5 shows the average values (g) of each drug product.

TABLE 5

|  | PEG MW of 200, combination ratio of 9:21 | PEG MW of 200, combination ratio of 1:29 | PEG MW of 1000, combination ratio of 9:21 | PEG MW of 1000, combination ratio of 1:29 | No addition of PEG |
|---|---|---|---|---|---|
| ND-membrane containing 50% kumazasa extract | 0 | 0.46 | 0.96 | 1.42 | 17.92 |
| FD-membrane containing 50% kumazasa extract | 0.68 | 7.97 | 3.30 | 2.98 | 16.78 |

With Table 5, the drug product containing PEG having a molecular weight of 200 at a combination ratio (PEG/chitosan) of 9:21 was bent to perpendicular to the ground with the lightest load; thus, it was confirmed to have a high plasticity.

What is claimed is:

1. A wound-dressing material comprising a product in the form of a sheet consisting essentially of chitosan as a base material and kumazasa extract, wherein the kumazasa extract is at an amount of 50 mass %.

2. The wound-dressing material according to claim 1, wherein the product has a sheet shape.

3. A wound-dressing material comprising a product in the form of a sheet consisting essentially of chitosan as a base material, kumazasa extract and polyethylene glycol, wherein the kumazasa extract is at an amount of 50 mass %.

4. A method for manufacturing a wound-dressing material of claim 1, which comprises the steps: gelatinizing a mixture solution containing chitosan and kumazasa extract; and drying the resulting gel.

5. The method for manufacturing the wound-dressing material according to claim 4, wherein the gel is obtained by adding an acetic acid solution to the mixture solution.

6. The method for manufacturing the wound-dressing material according to claim 5, wherein the drying is performed by natural drying or freeze drying.

7. A wound-dressing material comprising a product in the form of a sheet consisting of chitosan as a base material and kumazasa extract, wherein the kumazasa extract is at an amount of 50 mass%.

* * * * *